United States Patent [19]
Nogami et al.

[11] Patent Number: 5,196,801
[45] Date of Patent: Mar. 23, 1993

[54] CAPACITANCE-TYPE FUEL SENSOR FOR SENSING METHANOL IN METHANOL-MIXED FUEL

[75] Inventors: Yasuhiro Nogami; Hisao Nunokawa, both of Tokyo; Toshio Hirota, Yokosuka, all of Japan

[73] Assignees: Calsonic Corporation, Tokyo; Nissan Motor Co., Ltd., Yokohama, both of Japan

[21] Appl. No.: 450,302

[22] Filed: Dec. 15, 1989

[30] Foreign Application Priority Data

Dec. 19, 1988 [JP] Japan .................. 63-164211

[51] Int. Cl.$^5$ .................. G01R 27/26; G01N 27/22
[52] U.S. Cl. .................. 324/663; 324/690; 324/449; 324/450; 73/61.43
[58] Field of Search .............. 324/446, 448, 449, 450, 324/663, 686, 690, 679, 672, 677, 689; 73/61.1 R, 61.43

[56] References Cited

U.S. PATENT DOCUMENTS

| | | | |
|---|---|---|---|
| 2,832,039 | 4/1958 | Hardesty | 324/450 |
| 3,215,900 | 11/1965 | Harvey | 317/123 |
| 3,314,005 | 4/1967 | Whitener | 324/448 |
| 3,368,147 | 2/1968 | Graham | 324/61 |
| 3,778,706 | 12/1973 | Thompson | 324/61 R |
| 3,882,381 | 5/1975 | Gregory | 324/679 X |
| 4,470,300 | 9/1984 | Kobayashi | 324/677 X |
| 4,510,436 | 4/1985 | Raymond | 324/672 X |
| 4,559,493 | 12/1985 | Goldberg et al. | 324/689 X |
| 4,789,822 | 12/1988 | Ohmatoi | 324/60 R |
| 4,939,467 | 7/1990 | Nogami et al. | 324/450 X |

FOREIGN PATENT DOCUMENTS

| | | | |
|---|---|---|---|
| 0141636 | 5/1985 | European Pat. Off. | |
| 0341675 | 11/1989 | European Pat. Off. | 324/663 |
| 56-138431 | 10/1981 | Japan | |
| 57-153245 | 9/1982 | Japan | |

*Primary Examiner*—Jack B. Harvey
*Attorney, Agent, or Firm*—Foley & Lardner

[57] ABSTRACT

A fuel sensor for sensing methanol in methanol-mixed fuel, which comprises a structure which defines a fuel passage through which the mixed fuel flows, an electrode assembly including a pair of probe portions which are exposed to the fuel passage, and an electric circuit causing the paired probe portions to exhibit positive and negative characteristics respectively in the mixed fuel. At least the positive probe portion is intimately covered with an electrically insulating film.

8 Claims, 4 Drawing Sheets

CAPACITANCE-TYPE FUEL SENSOR FOR SENSING METHANOL IN METHANOL-MIXED FUEL

BACKGROUND OF THE INVENTION

1. Field of the Invention

The present invention relates in general to fuel sensor, and more particularly to fuel sensors of a type which sense the mixing ratio of methanol in a mixture of gasoline and methanol.

2. Description of the Prior Art

For dealing with the energy crisis and air polution problem, it has been proposed to use as the fuel of automotive internal combustion engine a mixed fuel, such as a mixture of gasoline and methanol. Japanese Patent First Provisional Publication 56-138431 shows one of fuel injection type engine systems operated on such mixed fuel. In the engine system of this publication, a measure is employed in which for practically operating the engine on the methanol-mixed gasoline, the fuel injection amount and ignition timing are controlled in accordance with the mixing ratio of methanol in the mixed fuel, which ratio is measured by a fuel sensor operatively disposed in a fuel container.

The fuel sensor is of a capacitance type which comprises a pair of spaced electrode plates submerged in the fuel. The dielectric constant of the fuel is detected by measuring the capacitance established between the electrode plates, and the mixing ratio of methanol is derived from the dielectric constant.

In operation, a DC voltage is applied between the electrode plate for electrostatic charging therebetween. Thus, one of the electrode plates serves as a positive electrode and the other serves as a negative electrode. The signal representative of the capacitance established between the positive and negative electrode plate under electrostatic charging is transmitted through lead wires to a separate control circuit where subsequent signal conversion and processing are carried out.

However, due to its inherent construction, the fuel sensor as mentioned hereinabove has the following drawbacks.

That is, due to application of DC voltage to the electrode plates, the plates are subjected to a corrosion in the methanol-mixed fuel.

In fact, even when the electrode plates are constructed of a corrosion-resistant plate, such as, stainless steel, nickel-plated metal, chrome-plated metal or the like, electrocorrosion can not be avoided. Furthermore, as a result of the electrodialysis, ionized metal in the fuel is attached to the negative electrode plate causing a non-negligible change in the capacitance characteristic of the electrode plates. This, of course, induces a considerable error in measuring the mixing ratio of methanol in the mixed-fuel.

In addition to the above, the corrosion products in the fuel tend to clog the fuel piping of the engine system.

SUMMARY OF THE INVENTION

It is therefore an object of the present invention to provide a fuel sensor which is free of the above-mentioned drawbacks.

According to the present invention, there is provided a fuel sensor for sensing methanol in methanol-mixed fuel, which sensor comprises first means defining a fuel passage through which the mixed fuel flows; an electrode assembly including one pair of probe portions which are exposed to the fuel passage; and second means causing the paired probe portions to exhibit positive and negative characteristics respectively in the mixed fuel, wherein at least the positive probe portion is intimately covered with an electrically insulating film.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

Figure 1:
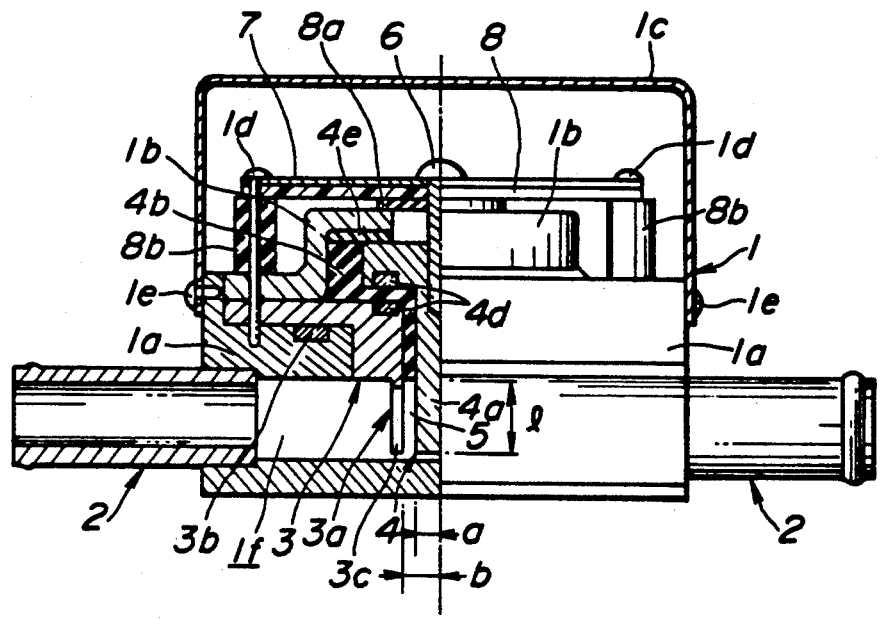
FIG. 1 is partially sectioned front view of a fuel sensor, which is a first embodiment of the present invention.
Figure 2:
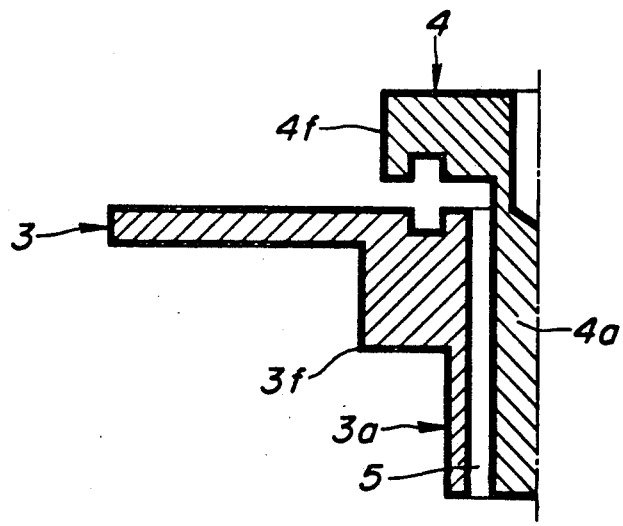
FIG. 2 is an enlarged sectioned view of an essential part of the first embodiment, showing films applied to surfaces of electrode.
Figure 3:
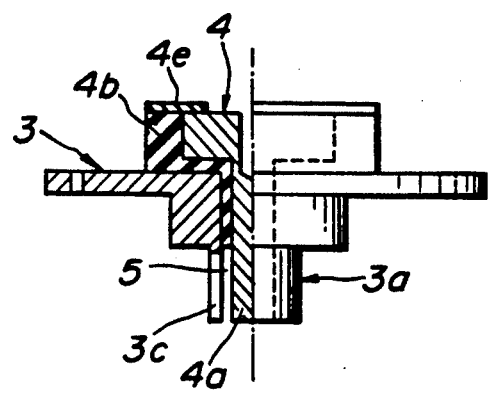
FIG. 3 is a partially sectioned front view of an electrode assembly mounted in the fuel sensor of the first embodiment.

Referring to FIGS. 1 to 6, particularly FIG. 1, there is shown a fuel sensor of a first embodiment of the present invention, which is applied to a fuel injection type automotive internal combustion engine system.

Denoted by numeral 1 is a housing of the sensor, which comprises a lower case 1a, an upper case 1b and a cover 1c. The upper case 1b is mounted on the lower case 1a and secured to the same by means of fastening screws 1d, and the cover 1c is secured to the lower case 1a by meas of fastening screws 1e in a manner to house therein the upper case 1b.

The lower case 1a has a fuel passage 1f formed therethrough. The fuel passage 1f has inlet and outlet portions to which respective pipes 2 are connected. One of the pipes 2 is connected to a fuel tube (not shown) which leads to fuel injection valves of the engine system.

Within the housing 1, there are arranged a pair of electrodes 3 and 4, one 3 being an outer (or negative) electrode and the other 4 being a center (or positive) electrode. These electrodes 3 and 4 have concentrically arranged probe portions 3a and 4a which are exposed to the fuel passage 1f of the lower case 1a. That is, the outer electrode 3 is mounted through a seal ring 3b to the lower case 1a having the cylindrical hollow probe portion 3a exposed to fuel passage 1f, while, the center electrode 4 is connected through an electrically insulating member 4e to the upper case 1b having the cylindrical solid probe portion 4a concentrically disposed within the cylindrical hollow probe portion 3a of the outer electrode 3. Thus, there is defined between the cylindrical hollow probe portion 4a and the cylindrical solid probe portion 4a a cylindrical space 5. An electrically insulating member 4b is disposed between the outer and center electrodes 3 and 4 to assure an electric insulation therebetween. Designated by numerals 4d are seal rings which are arranged having the insulating member 4b compressed therebetween.

As shown in FIG. 1, the fixing of the outer electrode 3 to the lower case 1a is effected by the afore-mentioned fastening screws 1d, while, the fixing of the center electrode 4 to the upper case 1b is effected by a fastening screw 6 which passes through the cover 1c.

Figure 4:
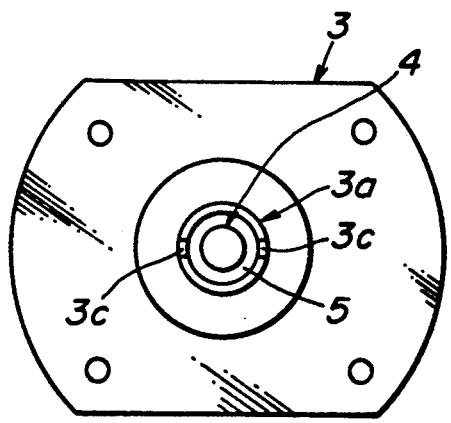
FIG. 4 is a bottom view of the electrode assembly.

As is understood from FIGS. 1 and 4, the cylindrical hollow probe portion 3a of the outer electrode 3 is formed at diametrically opposed portions thereof with respective slits 3c which are aligned with respect to the axis of the fuel passage 1f. Thus, the fuel following in the fuel passage 1f is easily fed to the cylindrical space 5.

Each of the electrodes 3 and 4 is constructed of aluminium or aluminium alloy. As is seen from FIG. 2. the outer surface of each electrode 3 or 4 is covered with an aluminium oxide film 3f or 4f. For this film covering, known anode oxidation method, chromic acid dipping method and phosphoric acid dipping method are usable.

If desired, in place of the aluminium oxide film, the outer surface of the electrode 3 or 4 may be covered with an organic film, such as fluoric resin film, acrylic resin film, epoxy resin film or the like. When such organic coating is employed, stainless steel is also usable as the material of the electrodes 3 and 4.

Furthermore, if desired, only the center (viz., positive) electrode 4 may covered with such an electrically insulating film.

As is shown in FIG. 1, an integrated circuit board whose base is denoted by numeral 8 is arranged within the cover 1c, which is supported on the lower and upper cases 1a and 1b by means of the afore-mentioned fastening screw 1d and 6. Electrically insulating spacers 8a and 8b are disposed between the base 8 and the upper case 1b, as shown. The base 8 has an integrated control circuit 7 printed thereon.

Figure 5:
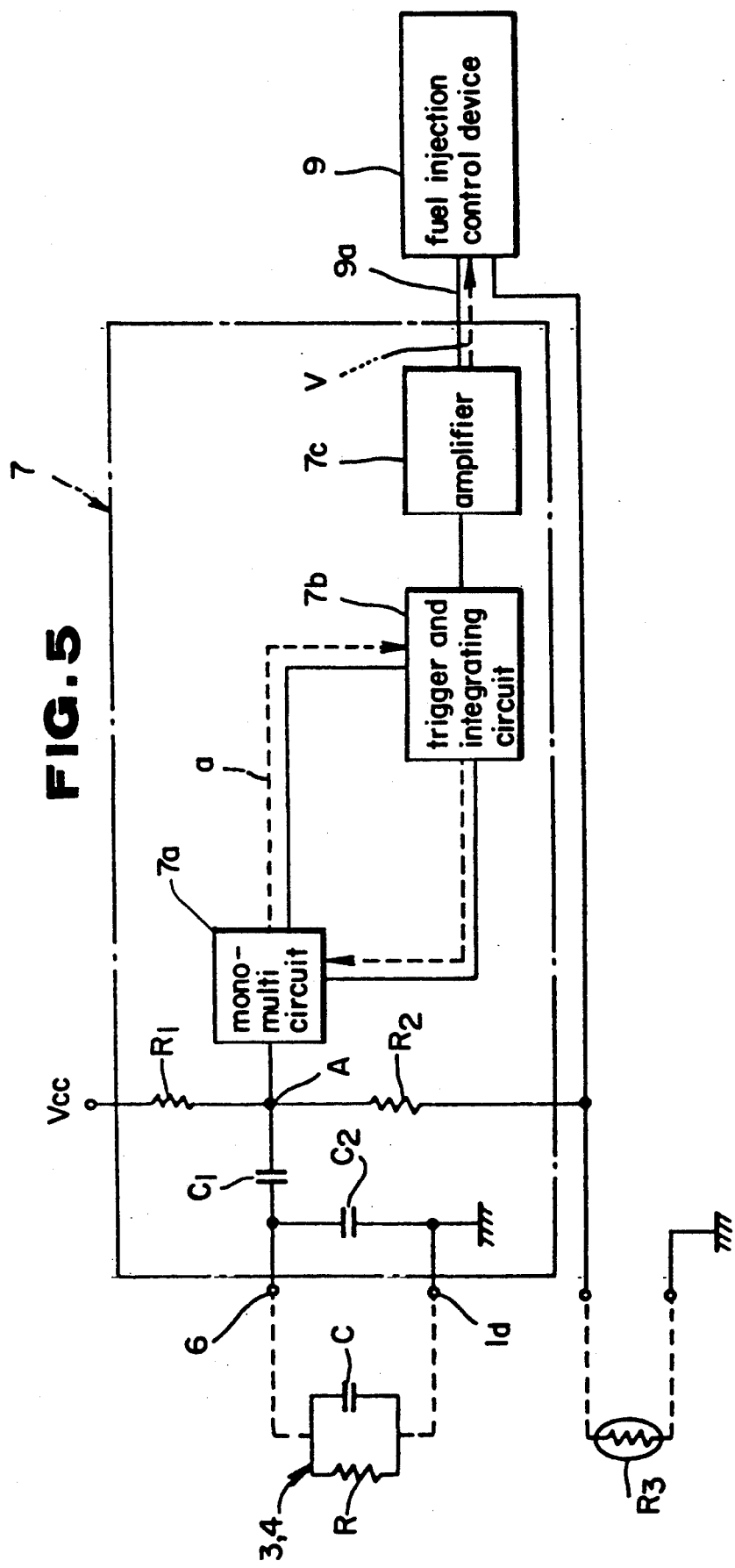
FIG. 5 is a control circuit installed in the fuel sensor of the invention.

The control circuit 7 functions to detect the capacitance established between the electrodes 3 and 4 and output an amplified voltage signal which varies in accordance with the methanol concentration in the mixed fuel. As is shown in FIG. 5, the control circuit 7 comprises condensers $C_1$ and $C_2$, resistor $R_1$ and $R_2$, a mono-multi (viz., monostable multivibrator) circuit 7a, a trigger and integrating circuit 7b and an amplifier 7c, which are connected in the illustrated manner. As shown, the junction between the condensers $C_1$ and $C_2$ is directly connected to the fastening screw 6, while the junction between the condenser $C_2$ and the grounds is directly connected to the fastening screw 1d. It is to be noted that the fastening screws 6 and 1d are constructed of a good conductive material, such as copper or the like. A thermistor $R_3$ is connected to the resistor $R_2$, whose resistance varies in accordance with its surrounding temperature. The thermistor $R_3$ is located in the cylindrical space 5 of the aforementioned electrodes 3 and 4.

The control circuit 7 is connected through lead wires 9a to a known fuel injection control device 9. The control device 9 functions to control the fuel injection amount, air-fuel ratio of air-fuel mixture fed to the engine proper and ignition timing in accordance with the voltage signal issued from the control circuit 7.

In the following, operation of the control circuit 7 will be described with reference to FIG. 5.

As shown in the drawing, the electrodes 3 and 4 are illustrated as a theoretical circuit which has both a capacitor C and a resistor R which are connected in parallel with the condenser $C_2$. The resistance of the resistor R is provided by the specified conductivity of methanol, which varies greatly depending on the amount of impurity, such as, ionized metal, water and the like, in the mixed fuel. In order to minimize the effect of the resistance of the resistor R, the period of charging and discharging an after-mentioned charging and discharging circuit is determined less than 1 $\mu$m second.

That is, the capacitor C, the resistor R and the mono-multi circuit 7a constitute the charging and discharging circuit. The trigger and integrating circuit 7b functions to issue a trigger signal to the mono-multi circuit 7a at a period of about 1 MHz and integrates a pulse signal "a" issued from the mono-multi circuit 7a.

When, thus, the mono-multi circuit receives the trigger signal, the junction denoted by reference "A" shows zero potential causing the capacitor C to discharge its energy. Thereafter, the capacitor C is gradually charged through the resistor R.

Upon receiving the trigger signal, the output signal from the mono-multi circuit 7a becomes high level.

When, due to charging of the capacitor C, the potential of the junction "A" reaches a threshold voltage, the mono-multi circuit 7a is returned to its stable condition thereby causing the output signal to become low level.

After a given time, another trigger signal is issued from the trigger and integrating circuit 7b to carry out a similar operation in the circuit. Such operation is repeated as long as the trigger signal is issued by the circuit 7b.

That is, in response to the output of the trigger signal, the mono-multi circuit 7a issues the output pulse signal "a" whose pulse duration is proportional to the time which is needed for charging the capacitor C.

The output pulse, signal "a" from the circuit 7a is integrated by the trigger integrating circuit 7b, and thus, the circuit 7b can issue an analog output in accordance with the charging time of the capacitor C. The analog output is amplified by the amplifier 7c to feed the fuel injection control device 9 with an amplified voltage signal "V". Based on the voltage signal "V" representative of the capacitance between the electrodes 3 and 4, the methanol concentration of the fuel is derived in the fuel injection control device 9.

In the following, operation of the fuel sensor of the first embodiment will be described.

In the fuel sensor, the dielectric constant of the mixed fuel is detected by measuring the capicitance established between the electrodes 3 and 4, and the methanol concentration in the fuel is derived from the dielectric constant.

That is, the capacitance Cf established between the electrodes 3 and 4 is expressed by the following equation.

$$Cf = 2\pi \times \epsilon \times l/\log(b/a) \tag{1}$$

wherein:
ε: dielectric constant of a fuel,
a: radius of cylindrical solid probe portion 4a of center electrode 4,
b: radius of cylindrical hollow probe portion 3a of side of the outer electrode 3, and
l: length of each probe portion 3a or 4a.

The dielectric constant "ε" is represented by the following equation.

$$\epsilon = k \times \epsilon_r \quad (2)$$

wherein:
$\epsilon_r$: relative dielectric constant, and
$k$: constant.

Furthermore, the dielectric constant "$\epsilon_n$" of a mixed fuel is expressed by the following equation.

$$\epsilon_n = (1-a)\epsilon_A + a\epsilon_B \quad (3)$$

wherein:
$\epsilon_A$: dielectric constant of fuel A,
$\epsilon_B$: dielectric constant of fuel B, and
$a$: mixing ratio of fuel B.

Thus, the capacitance Cf established in the mixed fuel is derived by combining the equation (1) and the equation (3). That is, by detecting the capacitance established between the two electrodes 3 and 4, the mixing ratio "$a$", viz., the methanol concentration in the mixed fuel can be obtained.

Experiments carried out by the inventors have revealed that the constant "k" in the equation (2) is about $9 \times 10^{-12}$ F. In the experiments, parallel electrode plates of given sizes were submerged in methanol whose relative dielectric constant is known (about 32.6) and the capacitance between the electrode plates was measured.

In the disclosed embodiment, the diameter of the fuel passage 1f is about 6 mm to 10 mm. This means that there is a limit in enlarging the size of the electrodes 3 and 4. Thus, if the probe portion of the electrode assembly has such a size that the diameter "a" of the center electrode is 0.0025 m, the internal diameter "b" of the outer electrode is 0.005 m and the length "l" of the probe portion is 0.01 m, the first equation (1) and the above-mentioned revealed constant "k" allow the capacitance "Cf" between the two electrodes to be about $1.9 \times 10^{-12}$ F which is very small.

It is now to be noted that the transmission of such small-energy electric signal to the control circuit 7 is carried out by electrically conductive fastening screws 6 and 1d each having a relatively short length. Thus, harmful effects of noises and floating capacitance on the measuring performance can be suppressed or at least minimized. Although the transmission of the output from the amplifier 7c to the fuel injection control device 9 is made through the lead wires 9a, such output is hardly affected by the noises and floating capacitance because the electric energy thereof is very higher than that of the noises and the floating capacitance.

As is described hereinabove, in the fuel injection control device 9, the methanol concentration of the fuel is calculated based on the output from the amplifier 7c, and at the same time, corrections to the fuel injection control and ignition timing control are carried out.

Figure 6:
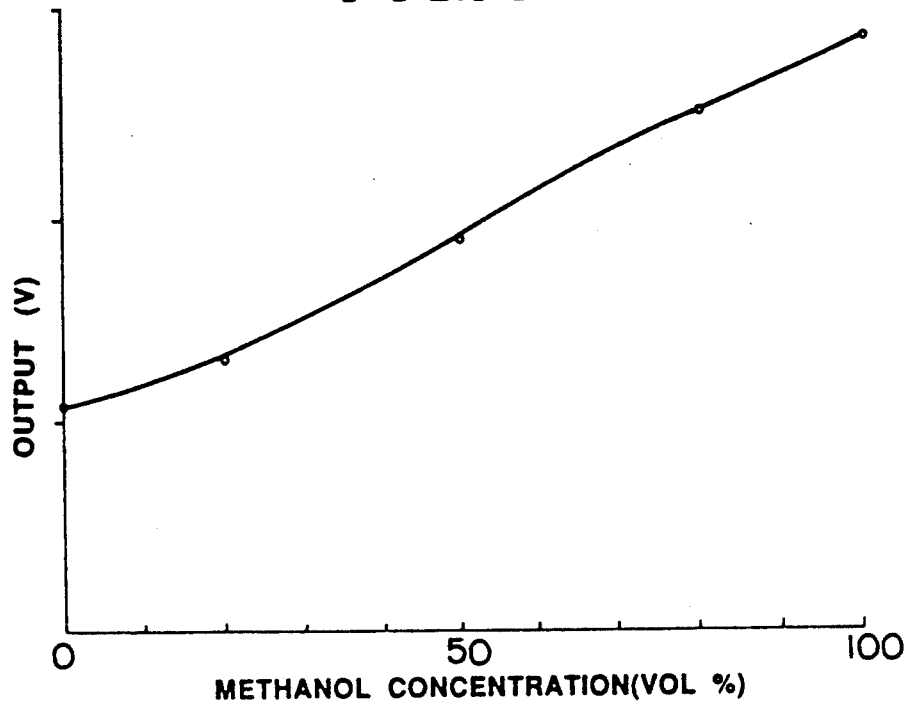
FIG. 6 is a graph showing the relationship between a methanol concentration in mixed fuel and amplified voltage output from the sensor.

FIG. 6 is a graph showing a relationship between the amplified voltage signal "V" issued from the amplifier 7c and the methanol concentration calculated in the fuel injection control device 9.

It is to be noted that, due to provision of the thermistor $R_3$ which is submerged in the fuel and connected to the junction "A" through the resistor $R_2$, the potential at the junction "A" is regulated in accordance with the temperature of the fuel. Thus, the measuring of methanol concentration in the fuel is achieved without being interrupted by the temperature change of the fuel.

Figure 7:
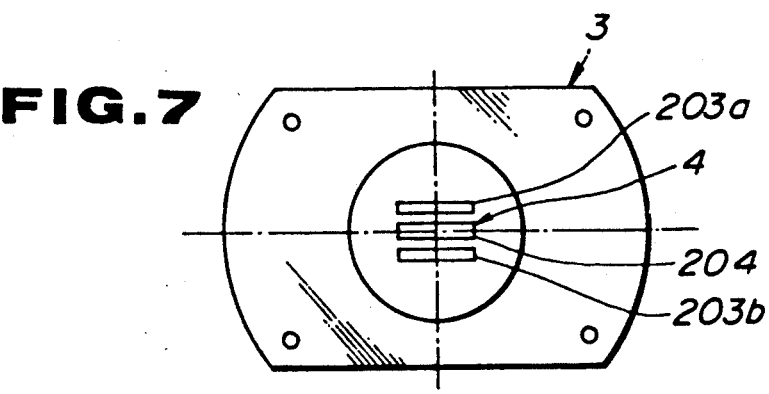
FIG. 7 is a view similar to 4, but showing an electrode assembly employed in a second embodiment of the invention.

Referring to FIG. 7, there is shown, but in a bottom view, an electrode assembly employed in a second embodiment of the present invention.

In this second embodiment, the outer electrode 3 has two flat probe portions 203a and 203b and the center electrode 4 has one flat probe portion 204. These three probe portions are arranged in parallel with the axis of the fuel passage 1f of the lower case 1a (see FIG. 1) having the center flat probe portion 204 spacedly put between the two side flat probe portions 203a and 203b. The remaining construction of the sensor of this embodiment is substantially the same as that of the above-mentioned first embodiment.

In the second embodiment, the capacitance "C" established between the outer and center electrodes 3 and 4 is represented by the following equation.

$$C = \epsilon \times S/d \quad (4)$$

In the following, advantages of the present invention will be itemed.

First, because each of the electrodes 3 and 4 is covered with an electrically insulating layer 3f or 4f, the afore-mentioned electrodialysis does not occur at the probe portions of them. Thus, the undesirable electrocorrosion of the probe portions can be avoided.

Second, because the electrodialysis does not occur, ionized metal is not produced. Thus, the negative electrode 3 is protected from collecting the ionized metal. Furthermore, because the fuel is free of the corrosion products, the fuel piping of the engine system is protected from clogging.

Third, since the electrode assembly and the integrated control circuit 7 are installed in a common housing 1, the length of electric conductors (viz., the fastening screws 6 and 1d) needed for electrically connecting these two electric parts can be shortened. This means that the harmful effects of noises and floating capacitance on the measuring performance of the sensor can be suppressed or at least minimized.

What is claimed is:

1. A fuel sensor for sensing a mixing ratio of a mixed fuel, said fuel sensor comprising:
 a housing;
 a structure disposed within said housing, said structure having a fuel passage formed therethrough;
 an electrode assembly disposed within said housing and secured to said structure, said electrode assembly including paired electrodes which have respective probe portions exposed to said fuel passage;
 an integrated circuit board arranged within said housing and on which an output control circuit is disposed, said output control circuit issuing an amplified voltage output which varies in accordance with a small information signal applied to an input portion of said output control circuit;
 at least two fastening screws connecting said integrated circuit board to said structure to form a tight mechanical connection therebetween, said fastening screws being constructed of electrically conductive material;
 wherein said fastening screws have respective upper portions directly contacting mutually insulated sections of said input portion of said output control circuit, and respective lower portions directly contacting said paired electrodes, respectively, wherein each of said probe portions of said electrode assembly is entirely covered with an electrically insulating film, wherein one of said probe portions is a cylindrical conductive solid member and the other probe portion is a cylindrical conductive hollow member and concentrically surrounds said solid member, and wherein said electrode assembly is so arranged that said probe portions extend perpendicular to a longitudinal axis of said fuel passage along which said mixed fuel flows.

2. A fuel sensor as claimed in claim 1, wherein each of said probe portions is constructed of one of aluminum and an aluminum alloy.

3. A fuel sensor as claimed in claim 2, wherein said electrically insulating film further comprises an aluminum oxide film which is provided by using a method selected from the group consisting of anode oxidation, chromic acid dipping and phosphoric acid method.

4. A fuel sensor as claimed in claim 1 wherein said electrically insulating film further comprises an organic film.

5. A fuel sensor as claimed in claim 4, wherein said organic film is selected from the group consisting of a fluoric resin film, acrylic resin film and epoxy resin film.

6. A fuel sensor as claimed in claim 1, wherein said hollow probe portion is formed at its diametrically opposed portions with aligned slits.

7. A fuel sensor as claimed in claim 1 wherein said fuel passage has a diameter of about 6 to 10 mm.

8. A fuel sensor for sensing a mixing ratio of a mixed fuel, said fuel sensor comprising:

a housing;

a structure disposed within said housing, said structure having a fuel passage formed therethrough;

an electrode assembly disposed within said housing and secured to said structure, said electrode assembly including paired electrodes which have respective probe portions exposed to said fuel passage;

an integrated circuit board arranged within said housing and on which an output control circuit is disposed, said output control circuit issuing an amplified voltage output which varies in accordance with a small information signal applied to an input portion of said output control circuit;

at least two fastening screws connecting said integrated circuit board to said structure to form a tight mechanical connection therebetween, said fastening screws being constructed of electrically conductive material;

wherein said fastening screws have respective upper portions directly contacting mutually insulated sections of said input portion of said output control circuit, and respective lower portions directly contacting said paired electrodes, respectively, wherein each of said probe portions of said electrode assembly is entirely covered with an electrically insulating film, and wherein each of said portions is constructed of stainless steel, and is entirely covered with an organic film which is selected from the group consisting of a fluoric resin film, acrylic resin film and an epoxy resin film.

* * * * *